United States Patent [19]

Hahn et al.

[11] 4,066,835
[45] Jan. 3, 1978

[54] PROCESS FOR PURIFYING THE WASTE WATER PRODUCED IN THE PROCESS OF PRODUCING ESTER PLASTICIZERS

[75] Inventors: Heinz-Dieter Hahn; Jurgen Weber, both of Oberhausen, Germany

[73] Assignee: Ruhrchemie AG, Oberhausen, Germany

[21] Appl. No.: 748,269

[22] Filed: Dec. 7, 1976

Related U.S. Application Data

[63] Continuation of Ser. No. 581,461, May 28, 1975, abandoned.

[30] Foreign Application Priority Data

May 31, 1974 Germany .............................. 2426448

[51] Int. Cl.$^2$ ....................... C07C 69/34; C07C 69/52
[52] U.S. Cl. ......................... 560/98; 210/71; 560/78; 560/191; 560/204
[58] Field of Search ....................... 210/71, 72; 203/34, 203/35, 39, 61; 260/499, 475 B, 485 S

[56] References Cited

U.S. PATENT DOCUMENTS

| | | | |
|---|---|---|---|
| 2,134,531 | 10/1938 | Punnett | 203/35 |
| 2,850,440 | 9/1958 | Shader | 203/35 |
| 3,397,121 | 8/1968 | Fitzgerald | 203/35 |
| 3,403,079 | 9/1968 | Olivier | 203/61 |
| 3,661,972 | 5/1974 | Biarnais | 260/499 |
| 3,816,485 | 6/1974 | Wechsler | 260/499 |
| 3,849,475 | 11/1974 | Biarnais et al. | 203/39 |

*Primary Examiner*—Tim R. Miles
*Assistant Examiner*—Frank Sever
*Attorney, Agent, or Firm*—Burgess, Dinklage & Sprung

[57] ABSTRACT

A process for removing organic components from the waste water effluent obtained in the production of an ester plasticizer through esterification of a polybasic aliphatic or aromatic carboxylic acid with an aliphatic alcohol in the presence of a sulfuric acid catalyst, which waste water contains an alkyl hydrogen sulfate or a dialkyl sulfate, esterification reactants and esterification products, which comprises:

A. Heating said waste water to a temperature above 200° C under the particular prevailing pressure; and B. Thereafter thermally or mechanically removing an organic phase from an aqueous phase.

11 Claims, No Drawings

PROCESS FOR PURIFYING THE WASTE WATER PRODUCED IN THE PROCESS OF PRODUCING ESTER PLASTICIZERS

This is a continuation of application Ser. No. 581,461, filed May 28, 1975, now abandoned.

BACKGROUND OF THE INVENTION

Field of the Invention

This invention relates to purification of waste water obtained during the production of an ester plasticizer through esterification of a polybasic carboxylic acid with an aliphatic alcohol. More particularly, this invention is directed to removing organic components from waste water and returning them to an esterification process whereby to leave behind water which can be readily purified so that it meets environmental standards and can be discharged. The present invention is particularly concerned with decreasing the biological oxygen demand of a waste water effluent from an ester plasticizer production process.

Discussion of Prior Art

Esters of aromatic or aliphatic polycarboxylic acids such as phthalic acid, trimellitic acid, adipic acid, sebacic acid, azelaic acid, with aliphatic alcohols such as 2-ethyl hexanol, isooctanol, isononanol or decanol are used in large amounts for plasticizing plastic materials, especially polyvinyl chloride. Of particular importance are the esters of phthalic acid with 2-ethyl hexanol (dioctylphthalate-DOP), isononyl alcohol (diisononyl phthalate-DINP), isodecyl alcohol (diisodecyl phthlate-DIDP) and butyl alcohol (dibutyl phthalate-DPB).

The reaction of the starting compounds, i.e., alcohol and acid or acid anhydride, can be accelerated by addition of catalysts, especially protonating compounds such as sulfuric acid, to an extent such that it is possible to operate under mild conditions of temperature. Apart from the addition of catalysts, it is usual in many cases to remove the water formed in the reaction from the equilibrium by means of an entraining agent.

When using sulfuric acid as the protonating catalyst, alkyl sulfuric acid and, in a very minor amount, dialkyl sulfates are generally formed from the starting alcohols in side reactions. Therefore, the raw esters also contain alkyl sulfuric acid in addition to residual amounts of carboxylic acids and alcohols which were not reacted as well as sulfuric acid.

In general, the raw esters are first neutralized with alkaline solutions such as sodium hydroxide or potassium hydroxide solution or with alkali metal carbonates, e.g., aqueous sodium carbonate solution. The resultant alkali metal salts of the organic acids including those of alkyl sulfuric acid are water-soluble and are separated with the aqueous phase. Sodium salts of alkyl sulfuric acids, partially esterified polycarboxylic acids and carboxylic acids are, as is known, surface-active at the corresponding molecular weight of the organic residue. Examples thereof include semi-esters of phthalic acid with monoalcohols having four or more carbon atoms and alkyl sulfates of octyl alcohol or alcohols of higher molecular weight. Due to the surface-activity of these compounds, larger amounts of otherwise sparingly soluble organic compounds, viz. the esters themselves and their starting compounds, are dissolved in the waste waters of the ester plasticizer production in addition to these compounds.

The content of organic materials in waste waters is usually characterized by the oxygen necessary for the reaction to form $CO_2$ and water. This value is known as the COD (chemical oxygen demand). For the waste water from the plasticizer ester production, COD values of 350 to 400 G oxygen per liter waste water are not unusual. Waste waters of this kind cannot be treated without a pretreatment in biological treatment means. In general, it is necessary to subject them to a prepurification by specific measures but at least to dilute them with large amounts of unloaded or uncontaminated water.

The waste waters from the ester synthesis also undesirably aggravate the separation of oils from other waste waters when passed jointly with the latter through oil removal basins. Therefore, problems in connection with environment protection have been encountered to an increased extent. In addition economic disadvantages through losses of valuable products have been experienced.

It is an object of this invention, therefore, to provide a process for the purification of effluent water obtained from ester plasticizer of production carried out employing a sulfuric acid catalyst. It is another object of this invention to recover organic materials dissolved in the waste water and to return them to the process without requiring expensive purification and separation techniques.

SUMMARY OF THE INVENTION

Broadly, this invention relates to a process for removing organic components from the waste water effluent obtained in the production of an ester plasticizer through esterification of a polybasic aliphatic or aromatic carboxylic acid with an aliphatic alcohol in the presence of sulfuric acid catalyst, which waste water contains an alkyl hydrogen sulfate or dialkyl sulfate, ester plasticizer reactants and products, which process comprises:

A. Heating said waste water to a temperature above 200° C under the particular prevailing pressure; and B. Thereafter mechanically removing by centrifuging or decanting an organic phase, leaving behind an aqueous phase.

Surprisingly, in accordance with this invention, it has been discovered that if the effluent waste water is heated to a temperature above 200° C under the particular prevailing pressure, there is formed an organic phase and aqueous phase. The organic phase can be removed by mechanical or thermal methods.

Generally speaking, the process of the present invention is carried out by heating the effluent waste water containing the alkyl hydrogen sulfate or dialkyl sulfate, esterification reactants and products at a temperature of at least 200° C, preferably between 210° and 250° C. Generally speaking, the heating can be carried out at a pressure between atmospheric and 40 atmospheric pressure. A convenient pressure is an autogenous pressure developed employing a closed vessel such as an autoclave. The effluent waste water is generally treated for a period of at least 15 minutes and generally up to 5 hours, depending upon the temperature employed. Preferably, the duration of the heat treatment is between 60 and 300 minutes. For example, at 220° C the desired reactions can be completed by heating the effluent waste water for a period of about 2 hours.

Effluent waste waters resulting from neutralization with an aqueous soda solution generally contain minor residual amounts of sodium carbonate in addition to larger amounts of sodium hydrogen carbonate. In accordance with this invention not only the sodium carbonate but also a portion of the sodium hydrogen carbonate is reacted to effect evolution of carbon dioxide. Accordingly, the reaction can also take place in the absence of chemicals having an alkaline reaction, e.g., in the presence of sodium hydrogen carbonate which has a neutral reaction. Thus, the reactions can differ by the fact of saponification of the esters in the presence of strong bases.

In carrying out the present invention under certain circumstances it is desirable from the standpoint of process engineering to suppress the $CO_2$ evolution, especially when purifying waste waters containing sodium carbonate. This is done to prevent the waste gases from being formed or to avoid an excessive increase in pressure during the reaction. In such cases, the $CO_2$ evolution can be prevented, and the $CO_2$ which would normally evolve can be bound within the reaction mixture by adding a stoichiometric amount of an alkaline solution such as a sodium or potassium hydroxide solution, thereby forming in the material being treated an alkali-carbonate.

After the process is conducted, the reaction mixture is cooled, preferably employing untreated effluent water flowing in countercurrent therewith. The resultant organic phase separates within a few minutes. Up to 150 kg of organic products are obtained per cubic meter of effluent water. Surprisingly, the ester plasticizers dissolved in the effluent water are hardly attacked. On the other hand, the alcohols present therein are split off almost quantitatively from the alkyl sulfates and from the semi-esters of the dicarboxylic acids and are separated with the organic phase. A small amount of olefins having partially been formed during the ester synthesis and being dissolved in the untreated effluent water can be obtained as by-product.

Where the waste water has a high alkali-hydrogen carbonate content it is generally desired to pretreat the waste water by the addition thereto of an alkali metal hydroxide in at least a stoichiometric amount.

The process can also be conducted by adding to the effluent water, such as after the separation of the organic phase, a mineral acid to adjust the pH of the aqueous phase to 3 to 3.5. Such process removes from the aqueous phase alkali metal salts of dicarboxylic acids. These materials were present in the effluent waste water in the form of the dicarboxylic acid prior to treatment with the mineral acid.

It has been found that after the separation of the organic phase, the effluent water still contains, among other things, the salts of the carboxylic acids, e.g., the disodium salts of phthalic acid. These dicarboxylic acids are sparingly soluble in water and can be readily separated from the aqueous phase by the aforesaid addition of mineral acid such as sulfuric acid, hydrochloric acid or phosphoric acid. The phthalic acid is largely separated at a pH of as low as 3.0 to 3.5. It can then be recovered by known methods, e.g., by filtration, centrifuging, decanting or the like.

Without considering the dicarboxylic acids, 85% of the organic materials are removed from the effluent water in the process according to the invention. A more than 98% separation of the organic materials is achieved when effecting the separation above of the carboxylic acids with subsequent filtration. The organic materials still remaining in the water may be separated without any difficulty by partial distillation.

There are several means for effecting the removal of the developing organic phase from the aqueous phase. These are generally mechanical methods. Mechanical methods for removing the organic phase include: decantation and centrifugation.

It will be realized that the heart of the present invention is the formation of an organic phase and an aqueous phase by heating the effluent waste water to a temperature of at least 200° C under the prevailing pressure. By whatever means the organic materials are removed, they can be reused in the ester plasticizer production, since the organic materials which are removed are almost exclusively starting materials, intermediate products and finished products of the ester plasticizer process. As such, they can readily be returned into the synthesis. The return of the materials recovered from the effluent water does not disadvantageously affect the ester plasticizer production and does not detract from the quality of the esters produced.

The production of the esters is usually carried out with an amount of alcohol in excess of the stoichiometric amount, generally a stoichiometric excess of 10 to 50%. Therefore, the separation of the excess alcohol from the ester produced is a measure which is necessary for processes of this kind. The separated alcohol is returned into the esterification stage either directly or after processing, e.g., by distillation. The alcohol recovered in the treatment of the effluent water may be separated without special measures and further used in known manner. Thus, in addition to the improvement of the quality of the waste water, the present invention leads to an extensive recovery of valuable products and, therefore, to an improvement of the yield based on the starting materials charged for the production of esters.

In order to more fully illustrate the nature of the invention and the manner of practicing the same, the following examples are presented:

EXAMPLES

The untreated process effluent water had the following characteristics on an average:
Flow rate: 400–500 liters/hr.
pH: 9.5
Sodium carbonate: 37.6 g/liter
Sodium hydrogen carbonate: 29.0 g/liter
COD: 360–380 g/liter The experiments described hereinafter were carried out with this effluent water. The composition of the waste water is typical of phthalic acid esters and other esters of aliphatic dicarboxylic acid and aliphatic alcohols.

EXAMPLE 1

Into a 5 liter autoclave with stirrer were introduced 3.3 liters of effluent water having the composition mentioned above. Then the autoclave was rapidly heated to the temperature given in the following table and maintained at this temperature for 2 to 5 hours. The pressure in the autoclave increased as the rate of conversion progressed. The increase in pressure could be reduced by adding 45% sodium hydroxide solution (see column 2 of the Table). After termination of the reaction time, the reaction mixture was cooled to room temperature, depressurized and drained from the autoclave. The upper organic phase was separated, weighed and analyzed by gas chromatography. The aqueous phase was examined for residual contaminations. The results are given in the following Table.

| Experiment | 1 | 2 | 3 | 4 | 5 |
|---|---|---|---|---|---|
| Quantity of waste water (liters) | 3.3 | 3.3 | 3.3 | 3.3 | 3.3 |
| Temperature(° C.) | 210 | 210 | 210 | 200 | 220 |
| Duration (hours) | 5 | 5 | 5 | 5 | 2 |
| Maximum pressure (kgs./sq.cm.g.) | 33 | 25 | 36 | 28 | 41 |
| Stirring | no | yes | yes | yes | yes |
| 45% NaOH added (g. per batch) | — | 150 | — | — | — |
| Quantity of orgnaic products (g.) | 355 | 362 | 364 | 204 | 360 |

| Experiment | 1 | 2 | 3 | 4 | 5 |
|---|---|---|---|---|---|
| Composition of the organic product | | | | | |
| Hydrocarbons | 4.7 | 4.8 | 4.3 | 5.3 | 4.6 |
| Olefin | 33.7 | 27.8 | 29.6 | 25.6 | 31.0 |
| Alcohol | 57.3 | 66.1 | 60.6 | 64.5 | 58.8 |
| Esters | 3.9 | 1.0 | 5.4 | 4.2 | 5.4 |
| Other organic compounds | 0.4 | 0.3 | 0.2 | 0.4 | 0.4 |
| Characteristics of the aqueous phase | | | | | |
| pH | 7.9 | 8.1 | 7.5 | 8.5 | 8.1 |
| $Na_2CO_3$ content (g./liter) | 1.1 | 4.0 | 0.4 | 3.0 | 1.7 |
| $NaHCO_3$ content (g./liter) | 36.5 | 53.2 | 29.1 | 39.3 | 34.8 |
| COD (g./liter) | 63 | 51 | 52 | 99 | 52 |

The aqueous phase of experiment 3 was acidified with sulfuric acid to pH 3.0. The phthalic acid was immediately precipitated in crystalline form. After filtration, the water had a COD of 6.0 g/liter. In part of the further experiments, COD values of 2.5 to 3.0 g/liter were even found.

EXAMPLE 2

3.3 liters of the effluent water were mixed with 60 g of concentrated sulfuric acid, i.e., with the amount which converts the sodium carbonate present in waste water into sodium hydrogen carbonate. The solution was then treated in the manner described in Example 1 for 3 hours at 220° C. The yield of organic materials was 356 g. The organic product had the following composition:
Hydrocarbon: 4.5%
Olefin: 28.6%
Alcohol: 61.9%
Ester: 4.8%
By-products: 0.2%

EXAMPLE 3

Into a 1 cu.m. pressure reactor filled with a tower packing of stainless steel were pumped 500 liters of the waste water having the composition mentioned above. The water was previously preheated under pressure to 230° C. No further heat was supplied to the reactor.

Upon completion of the reaction, the reaction mixture was cooled with untreated waste water and thereafter with cooling water in countercurrent flow relation and depressurized to atmospheric pressure. In a phase separator arranged downstream of the reactor, the organic phase was separated from the aqueous phase and returned into the esterification process. Organic product having the following composition was recovered at a rate of 56.1 kg/hr:
Hydrocarbon: 4.3%
Olefin: 29.5%
Alcohol: 60.6%
Ester: 5.5%
Non-specified by-products: 0.1%

What is claimed is:
1. A process for the preparation of an ester plasticizer and the reduction of the chemical oxidation demand of the waste water obtained thereby which comprises
   a. reacting a polybasic aliphatic or aromatic carboxylic acid with an alcohol in the presence of sulfuric acid;
   b. thereafter neutralizing the raw esters with an alkaline solution thereby forming a first organic phase and a first aqueous phase;
   c. separating said first aqueous phase from said first organic phase;
   d. heating said first aqueous phase at a temperature of at least 200° C at the prevailing pressure thereby forming a second aqueous phase and a second organic phase which is immiscible with said second aqueous phase and which does not redissolve in said second aqueous phase upon cooling; and
   e. physically separating said second organic phase from said second aqueous phase by centrifuging or decanting.
2. A process according to claim 1 wherein the waste water effluent is heated at a temperature between 210° and 250° C.
3. A process according to claim 2 wherein the heating of the water is carried out at a pressure of atmospheric up to 40 atmospheres.
4. A process according to claim 2 wherein heating of the water up to a temperature of 200° C is carried out of the water up to a temperature of 200° C is carried out under autogenous pressure.
5. A process according to claim 1 wherein subsequent to the heating of the water effluent at a temperature above 200° C there is added to the aqueous phase a mineral acid in an amount sufficient to adjust the pH of the aqueous phase to 3 to 3.5 whereby to remove from said aqueous phase alkali metal salt of the dicarboxylic acid.
6. A process according to claim 1 wherein the organic phase is returned to a process for the preparation of an ester of a polybasic acid by esterification with an aliphatic alcohol.
7. A process according to claim 1 wherein the heating of the water is carried out at a pressure of atmospheric up to 40 atmospheres.
8. A process according to claim 1 wherein heating of the water up to a temperature of 200° C is carried out under autogenous pressure.
9. A process according to claim 1 wherein the water which is treated contains the organic components dissolved therein.
10. A process for removing an organic component from a single phase aqueous effluent obtained by the esterification of a polybasic aliphatic or aromatic carboxylic acid with an aliphatic alcohol in the presence of sulfuric acid, which water contains an alkyl hydrogen sulfate or a dialkyl sulfate, ester and unreacted reactants, which process consists essentially of:
   A. Heating said effluent to a temperature above 200° C under the particular prevailing pressure thereby forming an organic phase and an aqueous phase from said effluent, which do not redissolve into each other upon cooling thereof; and
   B. Thereafter mechanically removing by centrifuging or decanting said organic phase from said aqueous phase.
11. A process according to claim 10 wherein the organic components are dissolved in said water.

* * * * *

UNITED STATES PATENT AND TRADEMARK OFFICE
CERTIFICATE OF CORRECTION

PATENT NO. : 4,066,835
DATED : January 3, 1978
INVENTOR(S) : Heinz-Dieter Hahn et al It is certified that error appears in the above-identified patent and that said Letters Patent are hereby corrected as shown below:

[75] Inventors, Title page, "Jurgen" should read -- Jürgen --.

Column 3, line 67, after "separation" insert -- described --.

Column 5, line 10, "orgnaic" should read -- organic --.

Column 5, line 18, column 3 in table, "60.6" should read -- 60.5 --.

Column 6, lines 28-29, after "out" delete "of the water up to a temperature of 200°C is carried out".

Signed and Sealed this

Sixth Day of June 1978

[SEAL]

Attest:

RUTH C. MASON
*Attesting Officer*

DONALD W. BANNER
*Commissioner of Patents and Trademarks*